United States Patent
Choi et al.

(10) Patent No.: US 8,022,090 B2
(45) Date of Patent: *Sep. 20, 2011

(54) VITAMIN C COMPOSITION STABILIZED WITH CATIONIC MATERIAL, ANIONIC MATERIAL AND CAFFEIC ACID DERIVATIVE

(75) Inventors: Min Hee Choi, Choongcheongnam-do (KR); Gi Woong Ahn, Suwon-si (KR); Byoung Kee Jo, Anyang-si (KR)

(73) Assignee: The Faceshop Korea Co., Ltd, Seoul (KR)

( * ) Notice: Subject to any disclaimer, the term of this patent is extended or adjusted under 35 U.S.C. 154(b) by 149 days.

This patent is subject to a terminal disclaimer.

(21) Appl. No.: 11/951,087

(22) Filed: Dec. 5, 2007

(65) Prior Publication Data

US 2008/0319060 A1    Dec. 25, 2008

(30) Foreign Application Priority Data

Jun. 19, 2007  (KR) .................... 10-2007-0059739

(51) Int. Cl.
*A61K 31/41* (2006.01)
*A61K 31/4155* (2006.01)
*C07D 249/08* (2006.01)

(52) U.S. Cl. .................. 514/383; 548/262.2; 548/263.2

(58) Field of Classification Search .............. None
See application file for complete search history.

(56) References Cited

U.S. PATENT DOCUMENTS

| | | | |
|---|---|---|---|
| 2004/0106529 A1* | 6/2004 | Fack et al. ............ | 510/119 |
| 2005/0154054 A1* | 7/2005 | Zielinski et al. ............ | 514/474 |

FOREIGN PATENT DOCUMENTS

TW        434262 B   *   5/2001

OTHER PUBLICATIONS

PDF document of 2 websites regarding Red Clover: (http://www.umm.edu/altmed/articles/red-clover-000270.htm and http://indigo-herbs.co.uk/acatalog/Red_Clover_Flowers_Info.html) accessed Jun. 2, 2010.*

* cited by examiner

*Primary Examiner* — Sharmila G. Landau
*Assistant Examiner* — Kevin S Orwig
(74) *Attorney, Agent, or Firm* — John K. Park; Park Law Firm

(57) ABSTRACT

The present invention relates to a composition containing vitamin C. The composition according to the present invention includes cationic material and anionic material as a primary stabilizing agent of the vitamin C; and a caffeic acid derivative as a secondary stabilizing agent of the vitamin C. The caffeic acid derivative is water-soluble and, preferably, a new caffiec acid derivative as denoted by the chemical formula 1 below is used. According to the present invention, the cationic material and the anionic material generate an electrical double layer to stabilize the vitamin C primarily; water-soluble caffeic acid derivative stabilizes the vitamin C secondarily. Accordingly, the vitamin C is stabilized double so that the vitamin C is protected from being oxidized by air, heat and moisture.

[Chemical formula 1]

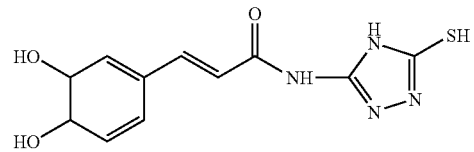

7 Claims, No Drawings

VITAMIN C COMPOSITION STABILIZED WITH CATIONIC MATERIAL, ANIONIC MATERIAL AND CAFFEIC ACID DERIVATIVE

CROSS-REFERENCE TO RELATED PATENT APPLICATIONS

This application claims the benefit of Korean Patent Application No. 10-2007-0059739, filed on Jun. 19, 2007, in the Korean Intellectual Property Office, the disclosure of which is incorporated herein in its entirety by reference.

BACKGROUND OF THE INVENTION

1. Field of the Invention

The present invention relates to a composition containing a vitamin C, more particularly, relates to a composition capable of protecting the vitamin C effectively by stabilizing the vitamin C double.

2. Description of the Related Art

It is well-known that a vitamin C shows strong antioxidant effect, anti-aging effect by the promoting capacity for the collagen biosynthesis, whitening effect by the restraining capacity against the melanin generation. However, an L-Ascorbic acid of vitamin C has a problem that it is easily oxidized at the external environment as like moisture, heat, light, air, etc, so that it becomes lost its titer and it becomes decomposed.

It is known that a dihydroascorbate radical, which is an oxidation intermediate, is generated by the dissociation of the hydrogen ions, where 2 electron-transfer processes are occurred serially. It is known that dihydroascorbate radical has powerful reactivity. The dihydroascorbate radical acts as 2 moleculars by itself to combine with the vitamin C, which is a molecular, thereby digydroascorbate acid is generated. This oxide of the vitamin C has a side-effect to damage the skin. And this oxide of the vitamin C has a problem to stimulate the skin when it is applied to the skin because it has structurally strong acidity. Because vitamin C can be oxidized easily in the alkalic aqueous solution, vitamin C can lost its color or ruined easily if it is placed on this environment in the process of maintenance and manufacture, To solve the defect of the vitamin C, that is, instability and stimulation in various environments, various vitamin C derivatives have been developed and these developed vitamin C derivatives are applied widely over grocery, pharmacy, medicine and cosmetics. However, these vitamin C derivatives have a problem that they are inferior to the pure vitamin C in effectiveness.

Also a method to add antioxidant agent, a method to stabilize the vitamin C in multiple emulsifying agents, a method to stabilize the vitamin C in an aqua emulsifying agent, a method to restrain the oxidation of vitamin C by coating, etc have been provided. However, these methods are not appropriate for the formulation of the cosmetic material because they do not show enough stability and effectiveness and because titer of the vitamin C becomes decreased as time goes. (U.S. Pat. No. 4,938,969, EP 0533667 B1)

Thus, there is a great need to develop stabilizing technique of vitamin C in order that skin activation capacity of vitamin C can be applied to the skin well.

SUMMARY OF THE INVENTION

An object of the present invention is to provide a composition capable of stabilizing vitamin C effectively thereby, skin activation capacity of vitamin C can be applied to the skin well thus good anti-aging effect and whitening effect can be achieved by regeneration of cell in the skin and increase of collagen synthesis.

A composition according to the present invention includes:
a vitamin C;
a cationic material and a anionic material as a primary stabilizing agent of the vitamin C; and
a caffeic acid derivative as a secondary stabilizing agent of the vitamin C.

It is preferable that the vitamin C is contained as much as 0.1~20 WT % (percently weight) with respect to the total weight of the composition and the cationic material and the anionic material are contained as much as 0.05~10 WT % with respect to the total weight of the composition.

It is preferable that the caffeic acid derivative is water-soluble and a new caffeic acid derivative as denoted by the chemical formula 1 below is used.

[Chemical formula 1]

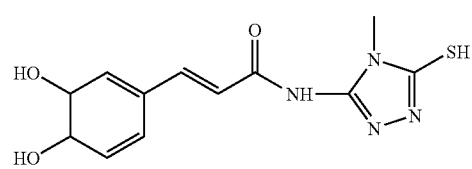

The composition according to the present invention can be selected from the group of compositions such as cosmetic material (cosmetics), medical material (medicine), food (groceries), etc. it is preferable that the composition according to the present invention has formulation of O/W cosmetic material composition.

According to the present invention, the cationic material and the anionicmaterial generate anelectrical double layer to stabilize the vitamin C primarily, a water-soluble caffeic acid derivative as denoted by the chemical formula 1 above stabilizes the vitamin C secondarily. Accordingly, the vitamin C is stabilized double so that the vitamin C is protected from being oxidized by air, heat and moisture thus activity of the vitamin C in the skin is increased effectively.

Additional aspects and/or advantages of the present invention will be set forth in part in the description which follows and, in part, will be obvious from the description, or may be learned by practice of the invention.

DETAILED DESCRIPTION OF THE INVENTION

Hereinafter the composition according to the present invention is described in detail.

By the result of repeated study of the inventors of the present invention to solve the instability problem of the vitamin C, the inventors becomes to know that a cationic material and a anionic material generate an electrical double layer to stabilize the vitamin C and thus oxidation of the vitamin C can be protected when the cationic material and the anionic material are contained together as oxidation stabilizing agents. The present invention can be completed by identifying that the vitamin C can be stabilized more effectively when a caffeic acid derivative is contained, and more particularly, powerful antioxidant power can be achieved when a new caffeic acid derivative as denoted by the chemical formula 1 above is used as the caffeic acid derivative.

The phrase "To stabilize vitamin C" in the present invention means to protect the phenomenon where titer decreases and color/smell changes by the oxidation when the vitamin C is exposed in the air or when it is existed in the water solution.

Vitamin C which the inventors of the present invention try to stabilize is a representative water-soluble pure vitamin. It is white powder type in dried powder state and it exists widely in natural world. Vitamin C is a common material which can be synthesized in the body of the plant and animal. However, unfortunately, fishes and primates including a human being cannot synthesize the vitamin C in his body. According, all lives including humans, who do not have mechanism to synthesize the vitamin C in the body, should supply necessary vitamin C through the ways such as ingestion of food. Because vitamin C can maintain its stability when it is a dried power, there is no worry about change in quality within the period of circulation of goods when it is made in the forms of dried medicine capsule, pouch or an additive for a snack. Thus, there is not a problem in making product. There is no difficulty in making product as long as vitamin C is packed, but there is a problem that titer decreases and color and smell changes when vitamin C is exposed to the air or when vitamin C is in the water-solution state.

Generally, cosmetic composition is based on liquid state formulation such as skin lotion, essence, cream, etc in most cases, various materials such as various additive, weighting material are contained, and the period of circulation of goods is relatively long within 1~3 years. In order to make vitamin C to cosmetic material, actual stabilization method to overcome the instability must be devised. Color of the vitamin C changed or destructed in quality varies to dark-brown over yellow and brown according to the degree of the destruction. This change in color happens to be recognized by customers as a change in color by the change in quality of all the materials in the cosmetic in the period of circulation. So the change in color can be a condition of dissatisfaction, refund, exchange so that it decreases marketability heavily.

The composition according to the present invention contains vitamin C and further it contains at least a cationic material, an anionic material and a caffeic acid derivative. The cationic material and the anionic material act as a primary stabilizing agent and the caffeic acid derivative acts as a secondary stabilizing agent, thus the vitamin C is stabilized double.

Vitamin C is dissolved in the water easily and it is transferred to a negative ion. At this time, the cationic material combines to the vitamin C to stabilize, the anionic material combines to this cationic material to separate the vitamin from the water and to absorb ultraviolet ray and thus it is protected that the vitamin C is decomposed by UV ray, air, and light. That is, the cationic material and the anionic material generate an electric double layer to protect the vitamin C from being oxidized.

As the cationic material, any material can be used as long as it can combine to the vitamin C that is transferred to the negative ion. Although it is not limited specially, chitosan, chitosan derivative, amino acid, polyquaternium, etc can be used as the cationic material. Especially, chitosan derivative is preferred.

The chitosan is a material which can be achieved by deacetylating chitin, which is a major component of the outer cover of the crustacea (for example crab, shrimp, etc) and the insects and the cell wall of the fungus. Because the chitosan is a high molecular substance, it is non-water-soluble. Thus its usage could be limited. Accordingly, a chitosan derivative, which has a characteristic of the chitosan and a characteristic of the water-solubility together, is preferred.

The chitosan derivative can make up the properties of the chitosan and it can be used in the wide pH range (pH 3 through pH 10). Especially it is good in adhesion capacity, durability, moisturizing capacity, membrane generating capacity, viscosity increasing capacity. Thus it is widely used over the cosmetics for hair including shampoo, rinse, treatment, hair-set lotion, etc and it is used as an aqua-additive of cream, liquid pack, foundation, soap, tooth paste, etc. Further, it is so good in antibiosis that it is used as a scaler to protect the generation of the plaque of the tooth by bacteria in the mouth and the decayed tooth.

Accordingly, it is preferable that the cationic material is selected from the chitosan derivatives, which has characteristics of the chitosan and which is effective to stabilize vitamin C as it acts as a catinic material.

As the chitosan derivative, one of polyoxyalkylene chitosan, carboxy methyl chitosan and N-2-hydroxy-propyl sulfonic acid chitosan or mixed one from more than 2 of them can be used.

As the anionic material, any material can be used as long as it can combine to the cationic material. For example, the anionic material can be selected from high molecules having a carboxy group, a sulfo group or amide bond. In detail, one of polymer, which is synthesized by adding a carboxyl group or a sulfo group to its terminal group or its side branch (for example, poly acrylic acid (PAA), polyvinyl sulphonic acid (PVSA) or their copolymer), high molecules derived from the polymer, poly aspartic acid and poly flutamic acid whose main chain is formed by amide bond, and copolymer of the poly aspartic acid and poly flutamic acid or mixed one from more than 2 of them can be used as the anionic material.

Polypeptide which has a good compatibility to the living body and a good biodegradability is used preferably.

Also, the caffeic acid derivative is contained to maximize the stability of the vitamin C. As the caffeic acid derivative, a new caffeic acid derivative provided in the present invention is usefully used. The new caffeic acid derivative is denoted by the chemical formula 1 above A chemical formula of a caffeic acid is C9H8O4 and molecular weight of the caffeic acid is 180.16. The caffeic acid is generally contained in the phemolic chemical compound and it is a yellow crystal which is easy to be dissolved in the water or alcohol. It has two hydroxyls and it relates to a cinnamic acid. The caffeic acid and the cinnamic acid are parts of carboxylic acid group, where a carbon is circulated, and it is a different chemical compound with caffeine. Although contained quality is different according to the kind of food, the caffeic acid is contained in fruit including coffee bean, pear and medicinal plants/vegetables including basil, thyme, verbena, tarragon, oregano, turmeric, wood betony, rosemary, dandelion, etc. The caffeic acid acts as a depressant against the production of cancer and it is known as an antioxidant in the interior and exterior of the living body. It is known that the antioxidant activity of the caffeic acid is superior to other antioxidant. Also, the caffeic acid can decrease the production of aflatoxin more than 95% and it can protect oxidation stress from being incurred.

According to the study of the inventors of the present invention, the caffeic acid has a powerful antioxidant activity but it is not useful to stabilize water-soluble vitamin C because it can not be dissolved easily in the water. By the result of repeated study of the inventors of the present invention about the chemical derivative to dissolve the caffeic acid in the water, a new caffeic acid derivative as denoted by the chemical formula 1 can be synthesized. The inventors can recognize that the caffeic acid derivative is highly water-soluble not only in the water but also in the alcohol. Also the inventors can recognize that the caffeic acid derivative can stabilize vitamin C easily and it has a powerful antioxidant activity.

The caffeic acid derivative of the chemical formula 1 can be named as [N-(5-Mercapto-1,2,4-triazole) 3,4-Dihydroxy Cinnamide].

Also, the caffeic acid derivative of the chemical formula 1 can be synthesized from the caffeic ethyl ester denoted by the chemical formula 2 below and triazole derivative denoted by the chemical formula 3 below.

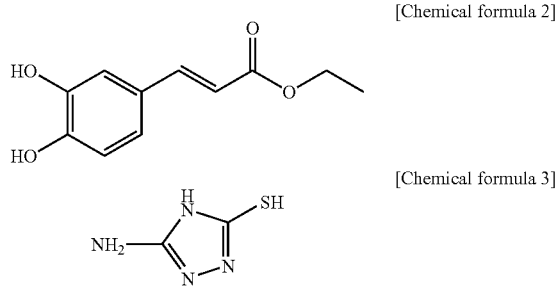

[Chemical formula 2]

[Chemical formula 3]

The caffeic acid derivative has powerful antioxidant activity thus it can be effectively applied to the skin and it can maximize the stabilization of the vitamin C. This caffeic acid derivative as denoted by the chemical formula 1 above is used as a antioxidant agent and/or a secondary stabilizing agent of the vitamin C in the composition according to the present invention.

The composition according to the present invention can be a composition of cosmetic material (cosmetics), medical material (medicine), food (groceries), etc. Especially, the composition according to the present invention can be composed by containing vitamin C; cationic material and anionic material as a primary stabilizing agent; a caffeic acid derivative as a secondary stabilizing agent beside a base component constituting the cosmetic material (cosmetics), medical material (medicine), food (groceries), etc. As the caffeic acid derivative, [N-(5-Mercapto-1,2,4-triazole) 3,4-Dihydroxy Cinnamide] as denoted by the chemical formula 1 above is preferable used.

It is preferable that the vitamin C is contained as much as 0.1~20 WT % with respect to the total weight of the composition. It is preferable that the primary stabilizing agent (the cationic material and the anionic material) is contained as much as 0.05~10 WT % with respect to the total weight of the composition. That is, it is preferable that the cationic material is contained as much as 0.05~10 WT % with respect to the total weight of the composition and the anionic material is contained as much as 0.05~10 WT % with respect to the total weight of the composition, respectively.

When the content of the vitamin C is less than 0.1 WT %, the effect due to the containing of vitamin C (skin whitening and wrinkle improvement effect according to the depression of melanin biosynthesis and oppression of collagen biosynthesis) is few. When the content of the vitamin C is more than 20 WT %, problems in stabilization of the formulation can be happened.

Further, it is more preferable that the cationic material and the anionic material are contained in the composition at same amount within the above described weight range.

It is not preferable that the content of the cationic material and the anionic material is used few (less than 0.05 WT %) because the effect to absorb the vitamin C can be degraded.

Further, it is also not preferable that the content of the catlionic material and the anionic material is used too much (more than 10 WT %) because precipitation can be happened by solubility.

It is difficult to achieve the effect of the present invention (stabilization of vitamin C, antioxidant activity, etc). When the content of the caffeic acid derivative is more than 10 WT %, problems in stabilization of formulation can be happened.

It is preferable that the caffeic acid derivative is contained as much as 0.05~10 WT % with respect to the total weight of the composition.

When the content of the caffeic acid derivative is less than 0.05 WT %, it is difficult to achieve the effect of the present invention (stabilization of vitamin C, antioxidant activity, etc). When the content of the caffeic acid derivative is more than 10 WT %, problems in the stabilization of the formulation can be happened.

In containing vitamin C, cationic material and anionic material into the composition according to the present invention, it is preferable that a solution containing double-stabilized vitamin C is prepared through the steps below in advance, and then the solution is contained into the base component of the composition.

In detail, after a solution containing double-stabilized vitamin C is prepared through the steps of: making a solution by dissolve vitamin C in the mixture of water and a polyhydric alcohol; making mixed liquor by adding a cationic material into the solution at the room temperature; making a primary stabilized vitamin C solution by adding a anionic material into the mixed liquor; and making a secondary stabilized vitamin C solution by adding a caffeic acid derivative of a new antioxidant agent, the secondary stabilized vitamin C solution is added and mixed to the base component of the composition.

The composition according to the present invention has a formulation of cosmetic material (cosmetics) composition preferably. In detail, the cosmetic material composition includes vitamin C, a cationic material and a anionic material beside common cosmetic material base components, and further it can include common container for example a stabilizing agent, a dissolvent agent, a colorant, a perfume, etc and a carrying agent. The composition according to the present invention can be made in the all the formulation which are made commonly in the cosmetic industry. Although it is not limited specially, toilet water, essence, lotion, paste, cleansing containing surfactant, cream, pack, gel, ointment, powder, patch, spray, etc can be included to the formulation.

When the formulation is one of paste, cream and gel, at least one selected from the group including animal oil, vegetable oil, wax, paraffin, cornstarch, tragacahth, cellulose derivative, polyethylene derivative, glycol, silicon, bentonite, silica, talc and zinc oxide can be used as a carrying agent component. For example, when the formulation of the cosmetic composition is toilet water or essence, a solvent, a solubilizing agent or an emulsifying agent can be used as a carrying agent and at least one selected from the group including water, ethanol, isopropanol, ethyl carbonate, ethyl acetate, benzyl alcohol, benzyl benzoate, prophylene glycol, 1,3-butylene glycol, oil, glycerol aliphatic ester, polyethylene glycol and aliphatic ester of sorbitan can be used.

When the formulation of the cosmetic composition is power or spray, at least one selected from the group including lactose, talc, silica, aluminum hydroxide, calcium silicate and polyamide powder can be used as a carrying agent. Especially, when the formulation of the cosmetic composition is spray, chlorofluorohydrocabon, prophane/butane or dimethylether can be used as a propellant, additively. When the formulation of the cosmetic composition is cleansing containing surfactant, at least one selected from the group including aliphatic alcohol sulfate, aliphatic estersulfate, sulphosuccinic acid monoester, isetionate, imidazolium derivative, methyltaurate, sarcosinate, aliphatic amide ether sulfate, alkylamid betain, aliphatic alcohol, fatty acid glyceride, fatty acid diethanolamide, vegetable oil, lanolin derivative and ethoxylated glycerol fatty acid ester can be used as a carrying agent.

Skin improving effect by the vitamin C can act effectively because the vitamin C is stabilized double in the cosmetic materials composition according to the present invention.

Accordingly, the cosmetic materials composition according to the present invention can improve the state of the skin, thus it is useful in skin whitening, wrinkle improving and skin elasticity improving.

The embodiments of the present invention will be described in detail. The embodiments described below are provided to describe the present invention in detail, and thus the skilled person in the art should understand obviously that the technical scope of the present invention cannot be limited by the description of these embodiments.

EXAMPLE OF PRODUCTION

<Synthesizing of the Caffeic Acid Derivative>

A caffeic ethylester denoted by the chemical formula 2 10 g is dissolved in ethanol 50 ml, a triazol derivate denoted by the chemical formula 3 5 g is applied, reflux stirring for 2 hours is performed and lastly it is cooled to the room temperature.

After strong hydrochloric acid 1 mL is applied, it is kept cool. By filtering the sediment and drying, the caffeic acid derivative 12 g (yield 80%) is achieved. By the result of the element analysis, it shows a proportions of "C 48.92 H 3.54 N 19.98 O 17.51; S 11.45" so that it is identified that the achieved caffeic acid derivative is the material ($C_{11}H_{10}N_4O_3S_1$ (278.33): C 47.47 H 3.62 N 20.13 O 17.24 S 11.52) which satisfies the chemical formula 1.

Example of Experiment 1

In order to identify solubility of the caffeic acid derivative achieved by the production example, 1 mg/mL, 10 mg/Ml and 100 mg/mL of the caffeic acid derivative are dissolved respectively while purified water and ethanol are used as solvent. A caffeic acid (Sigma, US), as a contrast agent, is dissolved with the same density and the same solvent and compared. The purified water and ethanol was placed at the water bath before the experiment to maintain their temperature at 25° C. The result of the experiment 1 is shown in table 1.

TABLE 1

(the result of solubility measurement)

| solvent | density (mg/mL) | solubility caffeic acid derivative | caffeic acid |
|---|---|---|---|
| purified water (25° C.) | 1 | dissolved completely | not dissolved |
|  | 10 | dissolved completely | not dissolved |
|  | 100 | dissolved completely | not dissolved |

TABLE 1-continued (the result of solubility measurement)

| solvent | density (mg/mL) | solubility caffeic acid derivative | caffeic acid |
|---|---|---|---|
| ethanol (25° C.) | 1 | dissolved completely | dissolved completely |
|  | 10 | dissolved completely | dissolved completely |
|  | 100 | dissolved completely | not dissolved |

As shown in table 1, it can be understood that the caffeic acid derivative according to the present invention can be dissolved by the purified water and the ethanol up to the density of 100 mg/mL. Also it can be understood that the caffeic acid of the contrast agent was not dissolved in the purified water and it could be dissolved in the ethanol up to 10 mg/mL.

Accordingly, it can be identified through the experiment 1 that the caffeic acid derivative according to the present invention is water-soluble and its solubility in the purified water and the ethanol is highly superior to the caffeic acid.

Example of Experiment 2

In order to identify antioxidant activity of the caffeic acid derivative achieved by the production example, a free radical scavenging activity test was performed. The free radical scavenging activity test was a modified test of Kim et al. (Ko. J. Pharmacogn., 24(4), 299-303 (1993) and a reagent of DPPH (1,1-diphenyl-2-picryhydrazyl, Sigma company), as a stable free radical, was used.

$150\mu\ell$ of the caffeic acid derivatives with various density are prepared. Those prepared caffeic acid derivatives are applied to 0.2 mM DPPH solution (when blank, ethanol is used), respectively and placed at the room temperature for 30 minutes. Experimental groups to test absorbency at 517 nm are established. Cases to use purified water are established as contrast groups. After measurement of absorbency with respect to the experimental groups and the contrast groups, elimination activation effect of free radical is achieved by using the equation 1 below. The result of the measurement is shown in table 2.

TABLE 2

[Equation 1]

$$\text{free radical elimination effect} = 100 - \frac{(\text{absorbancy of the expermental group}) - \text{blank absorbancy})}{\text{absorbancy of the contrast group}} \times 100$$

{The result of antioxidant activity measurement}

| caffeic acid derivative (ppm) | free radical elimination effect (%) |
|---|---|
| 3.125 | 22.0 |
| 6.25 | 39.1 |
| 12.5 | 64.8 |
| 25 | 87.9 |
| 50 | 95.1 |

It can be identified that the caffeic acid derivative has high free radical elimination capacity as shown in table 2.

Example of the Embodiment

Various cosmetic materials composition with components and proportions, as shown in table 3, are produced. In detail, the cosmetic materials composition includes vitamin 5 WT % (w/w) and the caffeic acid derivative 3 WT % (w/w) achieved by the above example of production beside common cosmetic materials composition.

Example of Comparison

Cosmetic materials composition with the same components and proportion without the caffeic acid derivative and the anionic material with respect to the cosmetic materials composition in the example of the embodiment was produced. Detailed component and proportion are shown in table 3.

TABLE 3

(component and proportion of cosmetic material composition)

| | content (WW %) | | | |
|---|---|---|---|---|
| component | example of embodiment | example of comparison 1 | example of comparison 2 | example of comparison 3 |
| 1. vaseline | 7.0 | 7.0 | 7.0 | 7.0 |
| 2. liquid paraffin | 10.0 | 10.0 | 10.0 | 10.0 |
| 3. beeswax | 2.0 | 2.0 | 2.0 | 2.0 |
| 4. polysolbate 60 | 2.0 | 2.0 | 2.0 | 2.0 |
| 5. soribitan sesquioleate | 2.5 | 2.5 | 2.5 | 2.5 |
| 6. squalane | 3.0 | 3.0 | 3.0 | 3.0 |
| 7. propylene glycol | 6.0 | 6.0 | 6.0 | 6.0 |
| 8. glycerin | 4.0 | 4.0 | 4.0 | 4.0 |
| 9. triethanolamine | 0.5 | 0.5 | 0.5 | 0.5 |
| 10. carboxyvinyl polymer | 0.5 | 0.5 | 0.5 | 0.5 |
| 11. tocopherol acetate | 0.1 | 0.1 | 0.1 | 0.1 |
| 12. vitamin C | 5.0 | 5.0 | 5.0 | 5.0 |
| 13. polyoxyalkylene chitosan | 1.0 | 1.0 | 1.0 | — |
| 14. poly aspartic acid | 1.0 | 1.0 | — | — |
| 15. caffeic acid derivative | 3.0 | — | — | — |
| 16. perfume, antiseptics | few | few | few | few |
| 17. purified water | To 100 | To 100 | To 100 | To 100 |

Example of Experiment 3

<Titer Measurement of Vitamin C>

In order to identify the titer maintenance capacity of the double-stabilized vitamin C according to the present invention, titer maintaining capacity was measured as follows. Supposing that initial titer of the composition according to the example of embodiment and example of comparison was 100, titer after 1 month was measured at the temperature 25° C. and 45° C., respectively. The result of the measurement was shown in table 4. For the measurement, Waters company Sunfire C185, 100A, 150×4.6 mm column was used. The wavelength of the detector was 254 nm, the moving phase of 25 mM KH2)04 buffer (pH2.5) was used and it was measured at the flow velocity of 0.6 mL/min.

TABLE 4

(comparison of titer of vitamin C)

| remarks | example of embodiment | example of comparison 1 | example of comparison 2 | example of comparison 3 |
|---|---|---|---|---|
| 25° C. | 99 | 90 | 72 | 60 |
| 45° C. | 90 | 78 | 50 | 23 |

It can be understood that the example of embodiment where vitamin C was stabilized double is more stable that example of comparison 1 where the caffeic acid derivative was not used, example of comparison 2 where vitamin C was by the cationic molecular only and example of comparison 3 where a stabilizing agent was not used as time goes, as shown in table 4.

Example of Experiment 4

<Test of the Stability of the Formulation>

In order to identify the stability of the formulation of the double-stabilized vitamin C according to the present invention, the stability of the formulation was measured as follows.

Cosmetic materials compositions according to the example of embodiment and example of comparisons were stored for 12 weeks in opaque glassy vessels at the thermostat of 45□ and then they were stored for 12 weeks in opaque glassy vessels at the refrigerator of 4□ with the light shielded completely. After then, variance of color and smell was measured in comparison.

The result is shown in table 5. The degree of variance of color and smell was evaluated by 6 ranks as follows.

0: no variance
1: varied few
2: varied a little
3: varied a lot
4: varied seriously
5: varied very seriously

TABLE 5

(comparison of the stability of the formulation)

| classification | stability of formulation | | | | | | | |
|---|---|---|---|---|---|---|---|---|
| | example of embodiment | | example of comparison 1 | | example of comparison 1 | | example of comparison 1 | |
| | 45° C. | 4° C. | 45° C. | 4° C. | 45° C. | 4° C. | 45° C. | 4° C. |
| variance in color | 0.5 | 0 | 1.8 | 1.0 | 2.0 | 1.7 | 4.8 | 5.5 |
| variance in smell | 0.3 | 0 | 0.9 | 0.3 | 1.0 | 0.5 | 1.5 | 0.8 |

It can be understood that the cosmetic materials composition according to the embodiment of the present invention was varied few at 45□.

By this, it can be understood that the double-stabilized vitamin C that is, the cationic material, the anionic material, the caffeic acid derivative and the vitamin C, is exist in the stabilized state in the formulation.

Based on the results of the example of experiments, some examples of formulations containing the caffeic acid derivative which stabilize vitamin C, which is very unstable in the water, according to the present invention are provides below. However, it should be noticed that this provision does not aim to limit the composition according to the present invention to formulations below.

Example of Formulation 1

<Soft Toilet Water (Skin Lotion)>

Soft toilet water (skin lotion) was produced according to the component and content as shown in table 6.

TABLE 6

(component and content of the example of the formulation 1)

| component | content (ww&) |
|---|---|
| vitamin C | 1.0 |
| caffeic acid derivative | 1.0 |
| polyoxyalkylene chitosan | 0.2 |
| poly aspartic acid | 0.2 |
| 1,3-butylene glycol | 6.0 |
| glycerin | 4.0 |
| oleyl alcohol | 0.1 |
| polysolbate 20 | 0.5 |
| ethanol | 15.0 |
| benzophenone-9 | 0.05 |
| perfume, antiseptics | few |
| purified water | to 100 |

Example of Formulation 2

<Nutrition Toilet Water (Milk Lotion)>

Nutrition toilet water (milk lotion) was produced according to the component and content as shown in table 7.

TABLE 7

(component and content of the example of the formulation 2)

| component | content (ww %) |
|---|---|
| vitamin C | 3.0 |
| caffeic acid derivative | 3.0 |
| polyoxyalkylene chitosan | 0.6 |
| poly aspartic acid | 0.6 |
| propylene glycol | 6.0 |
| glycerin | 4.0 |
| triethanolamine | 1.2 |
| tocopherol acetate | 3.0 |
| liquid paraffin | 5.0 |
| squalane | 3.0 |
| macadamianut oil | 2.0 |
| polysolbate 60 | 1.5 |
| soribitan sesquioleate | 1.0 |
| carboxyvinyl polymer | 1.0 |
| BHT | 0.01 |
| EDTA-2Na | 0.01 |
| perfume, antiseptics | few |
| purified water | to 100 |

Example of Formulation 3

<Nutrition Cream>

Nutrition cream was produced in common method according to the component and content as shown in table 8.

TABLE 8

(component and content of the example of the formulation 3)

| component | content (ww %) |
|---|---|
| vitamin C | 5.0 |
| caffeic acid derivative | 3.0 |
| polyoxyalkylene chitosan | 1.0 |
| poly aspartic acid | 1.0 |
| cetostearyl alcohol | 2.0 |
| glyceryl stearate | 1.5 |
| trioctanoin | 5.0 |
| polysolbate 60 | 1.2 |
| sorbitan stearate | 0.5 |
| squalane | 5.0 |
| liquid paraffin | 3.0 |
| cyclomethicone | 3.0 |
| BHT | 0.05 |
| delta-tocopherol | 0.2 |
| concentrate glycerin | 4.0 |
| 1,3-butylene glycol | 2.0 |
| santa gum | 0.1 |
| EDTA-2Na | 0.05 |
| perfume, antiseptics | few |
| purified water | to 100 |

Example of Formulation 4

<Massage Cream>

Massage cream was produced in common method according to the component and content as shown in table 9.

TABLE 9

(component and content of the example of the formulation 4)

| component | content |
|---|---|
| vitamin C | 3.0 |
| caffeic acid derivative | 5.0 |
| polyoxyalkylene chitosan | 0.6 |
| poly aspartic acid | 0.6 |
| propylene glycol | 2.0 |
| glycerin | 4.0 |
| carboxyvinyl polymer | 0.3 |
| ethanol | 7.0 |
| PEG-40 hydrogenated caster oil | 0.8 |
| triethanolamine | 0.3 |
| BHT | 0.01 |
| DDTA-2Na | 0.01 |
| perfume, antiseptics | few |
| purified water | to 100 |

Example of Formulation 5

<Pack>

Pack was produced in common method according to the component and content as shown in table 10.

TABLE 10

(component and content of the example of the formulation 5)

| component | content |
|---|---|
| vitamin C | 3.0 |
| caffeic acid derivative | 5.0 |
| polyoxyalkylene chitosan | 0.6 |
| poly aspartic acid | 0.6 |
| propylene glycol | 2.0 |
| glycerin | 4.0 |
| carboxyvinyl polymer | 0.3 |
| ethanol | 7.0 |
| PEG-40 hydrogenated caster oil | 0.8 |
| triethanolamine | 0.3 |
| BHT | 0.01 |
| DDTA-2Na | 0.01 |
| perfume, antiseptics | few |
| purified water | to 100 |

As described above, the cationic material and the anionic material generate an electrical double layer to stabilize the vitamin C primarily; water-soluble caffeic acid derivative stabilizes the vitamin C secondarily. Accordingly, the vitamin C is stabilized double so that the vitamin C is protected from being oxidized by air, heat and moisture. And further, the composition according to the present invention can activate application of vitamin C to various products (cosmetic materials and medical materials) because variance in color and smell of the vitamin C is protected. The vitamin C acts effectively to increase whitening effect and to protect skin-aging as the vitamin C is stabilized effectively.

What is claimed is:

1. A composition comprising:
   vitamin C;
   a cationic material and an anionic material as a primary stabilizing agent of the vitamin C; and
   a caffeic acid derivative as a secondary stabilizing agent of the vitamin C wherein the caffeic acid derivative is denoted by chemical formula 1 below

[Chemical formula 1]

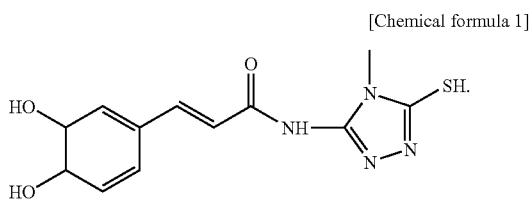

2. The composition in claim 1, wherein the vitamin C is contained in the amount of 0.1~20 WT % with respect to the total weight of the composition, the cationic material and the anionic material are contained in the amount of 0.05~10 WT % with respect to the total weight of the composition and the caffeic acid derivative is contained in the amount of 0.05~10 WT % with respect to the total weight of the composition.

3. The composition in claim 1, wherein the cationic material is carboxy methyl chitosan.

4. The composition in claim 1, wherein the anionic material is a poly peptide.

5. The composition in claim 1, wherein the caffeic acid derivative is synthesized using the caffeic ethyl ester as denoted by the chemical formula 2 below and the triazole derivative as denoted by the chemical formula 3 below

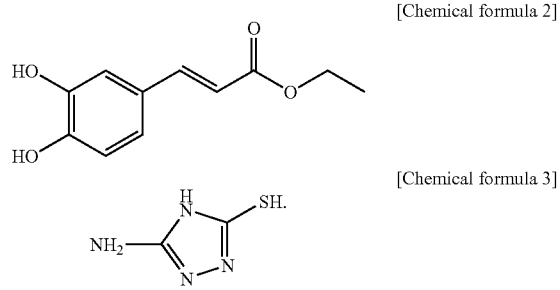

6. The composition in any one of claims 1 through 5, wherein the composition is a cosmetic material composition.

7. The composition in claim 6, wherein the composition has the formulation of a toilet water, essence, lotion, cream, pack, gel, ointment, powder, patch or spray.

* * * * *